(12) United States Patent
Cole et al.

(10) Patent No.: US 9,829,433 B2
(45) Date of Patent: Nov. 28, 2017

(54) IMAGING TECHNIQUES AND ASSOCIATED APPARATUS

(75) Inventors: Bryan E. Cole, Cambridgeshire (GB); Philip F. Taday, Cambridgeshire (GB); Anthony J. Fitzgerald, Cambridgeshire (GB)

(73) Assignee: TeraView Limited, Cambridge (GB)

( * ) Notice: Subject to any disclaimer, the term of this patent is extended or adjusted under 35 U.S.C. 154(b) by 1376 days.

(21) Appl. No.: 10/540,962

(22) PCT Filed: Jan. 12, 2004

(86) PCT No.: PCT/GB2004/000071
§ 371 (c)(1),
(2), (4) Date: Nov. 22, 2005

(87) PCT Pub. No.: WO2004/063726
PCT Pub. Date: Jul. 29, 2004

(65) Prior Publication Data
US 2006/0235621 A1   Oct. 19, 2006

(30) Foreign Application Priority Data
Jan. 10, 2003  (GB) .................................. 0300573.3

(51) Int. Cl.
| G01N 33/48 | (2006.01) |
| G01N 21/47 | (2006.01) |
| G01N 21/3586 | (2014.01) |
| G01N 21/3563 | (2014.01) |
| G06G 7/58 | (2006.01) |
| G01N 21/95 | (2006.01) |

(52) U.S. Cl.
CPC ..... G01N 21/4795 (2013.01); G01N 21/3563 (2013.01); G01N 21/3586 (2013.01); *G01N 21/9508* (2013.01)

(58) Field of Classification Search
None
See application file for complete search history.

(56) References Cited

U.S. PATENT DOCUMENTS 5,467,404 A   11/1995  Vuylsteke et al.

FOREIGN PATENT DOCUMENTS

| EP | 0727671 A2 | 8/1996 |
| EP | 0 828 162 A2 | 3/1998 |
| EP | 0864857 A1 | 9/1998 |
| GB | 2360186 A | 9/2001 |
| JP | 5-26919 A | 2/1993 |
| JP | 5 244508 A | 9/1993 |
| JP | 8-320254 A | 12/1996 |
| JP | 10-90065 A | 4/1998 |
| JP | 10-90174 A | 4/1998 |
| JP | 11-108845 A | 4/1999 |
| JP | 2000-135268 A | 5/2000 |
| WO | WO 99/63478 A1 | 12/1999 |
| WO | WO-00/75641 | 12/2000 |

OTHER PUBLICATIONS

Martin C. Nuss, "Chemistry is Right for T-Ray Imaging Laser, Microwave and Signal Processing Technologies a Perfect Blend for Applicatrons in Packaging, Security, and Quality Control" IEEE Circuits and Devices Magazine, IEEE, Inc. New York, vol. 12, No. 2, Mar. 1, 1996, pp. 25-30.

*Primary Examiner* — Eric S Dejong
(74) *Attorney, Agent, or Firm* — Blank Rome LLP (57) ABSTRACT

Imaging techniques of pharmaceutical preparations such as tablets are disclosed. The techniques combine the measurement of reflected/transmitted terahertz radiation originating from within the tablet and data analysis localized in frequency and time in order to enable a three dimensional image indicating composition to be obtained.

19 Claims, 11 Drawing Sheets

IMAGING TECHNIQUES AND ASSOCIATED APPARATUS

FIELD OF THE INVENTION

The present invention relates generally to the field of apparatus and methods for obtaining information about the chemical composition of a sample. More specifically, the present invention relates to imaging a pharmaceutical sample and obtaining three dimensional information about the composition of the sample using radiation in the infrared (IR) and Terahertz frequency range in the range from 25 GHz to 100 THz. However, in this type of imaging technology, all such radiation is colloquially referred to as THz radiation, particularly that in the range from 25 GHz to 100 THz, more particularly that in the range of 50 GHz to 84 THz, especially that in the range from 100 GHz to 50 THz.

BACKGROUND OF THE INVENTION

The production of pharmaceuticals is a costly and complex procedure. In general the procedure involves four key stages, namely:
 Drug Discovery
 Product Development
 Process Development for manufacturing the product; and
 Manufacture Drug discovery involves identifying polymorphs and their salts that may be pharmaceutically active. This involves a high throughput polymorph detection and screening process. Possible pharmaceutical candidates are identified in this screening, and these candidates then progress to the product development stage, where they undergo clinical trials. In the clinical trials one or more active components are combined with certain inert excipients, such as lactose and sucrose. The structure and distribution uniformity of the active ingredient(s) in the combined form is then assessed. For example, the composition is assessed in terms of how it is compressed and bound together in a dosage form. Various excipients can be trialled at this stage until the most suitable excipients are determined. Hence at this stage it is desirable to be able to image the chemical composition. It would be particularly desirable to obtain a three dimensional image in a short period of time and with a high throughput.

The process development stage evaluates how to process the one or more active components with the excipients on the production line. For example, where the active component is being formed into tablets, a suitable process needs to be developed for blending and compressing the components in a tablet press. This is a critical step in pharmaceutical development, as seemingly simple formulations with identical ingredients can perform radically differently depending upon how the ingredients are blended together. For example, it is not uncommon for active ingredients in a dosage form to be unevenly distributed and in clumps, particularly where the dosage concentration is low. This is undesirable, as the therapeutic value of the tablet often depends on the distribution of the active ingredient. This problem is compounded with pharmaceuticals containing highly active ingredients and also with those that are administered by complex delivery systems.

The final phase of the pharmaceutical development procedure is the manufacturing stage. At this stage it is desirable to monitor the composition of the products being manufactured in order maintain quality standards.

Therefore, at all of these stages in the pharmaceutical development process there is a need to be able to obtain information about the composition of a pharmaceutical product. There is also a need to be able to image the pharmaceutical product and obtain a three dimensional image of the composition of the product.

In particular there is a need for three dimensional mapping of pharmaceutical products, particularly highly toxic or reactive ones, in a non-invasive, efficient manner and with minimal contact.

It would also be desirable to have an approach with a high throughput and also to be able to monitor and control the quality of the composition in a short period of time.

Known techniques of assessing pharmaceutical compositions include performing tablet assays, which entail invasive sample preparation procedures such as tablet crushing, dissolution and chromatographic separation of active ingredients from excipients. These techniques are of limited value, however, as all the information on the physical state of the ingredients and how they relate to each other is effectively lost due to their invasive nature. In this regard, the quality of a formulation can be assessed via the structure of the matrix that evolves during the manufacturing process. Therefore it is desirable to have a technique that maintains the matrix structure.

A technique that has been used to assess tablet content uniformity involves staining the sample to generate image contrast between active ingredients and excipients. While this technique maintains the matrix structure, the staining process is invasive.

NIR spectroscopy has been used to image pharmaceuticals, as described in the article entitled "A near infrared view of pharmaceutical formulation analysis" by Lewis, Carroll and Clarke published in NIR News Vol. 12, No. 3 (2001). The technique however, is not able to readily provide an indication of how the active ingredients are heterogeneously distributed throughout the tablet, as only an image of the surface can be obtained.

Another approach uses Raman spectroscopy. This technique obtains Raman image data and applies multi-variant image processing thereto. This can provides a surface map indicating spatial distribution of ingredients. It is generally a better technique than NIR contrast enhancement approaches in that it is able to map active and excipient materials even when both are white powders. However, once again, only an image of the surface of the tablet can be obtained.

Therefore, both NIR and Raman spectroscopy are able to provide images identifying chemical specificity, but due to issues of scattering, they are not able to probe much below the surface of the sample.

Another problem with Raman spectroscopy is that it cannot be used on chemicals that fluoresce, as this masks the Raman signal. Further, high power illumination is a feature of Raman spectroscopy, and this can lead to heating and changes in chemistry of the sample being imaged.

Micro-computed tomography and magnetic resonance imaging are able to provide three-dimensional image information, but these techniques require long periods of time to produce an image.

It is desirable to have a technique that improves testing turnaround time, as this can save large amounts of money through a decrease in the time-to-market.

It is also desirable to provide an improved imaging technique that is able to provide a three dimensional composition representation.

BRIEF SUMMARY OF THE INVENTION

In one aspect, the present invention provides a method of generating a representation of the compositional distribution of a chemical sample as a function of depth, comprising:

irradiating the sample with radiation having a plurality of frequencies in the range from 25 GHz to 100 THz;
detecting radiation reflected from and/or transmitted by said sample to obtain a time domain waveform;
obtaining frequency data as a function of time from the time domain waveform;
deriving the representation from the frequency data.

In another aspect, the present invention provides a method of generating a representation of the granularity of a chemical sample as a function of depth, comprising:
irradiating the sample with radiation having a plurality of frequencies in the range from 25 GHz to 100 THz;
detecting radiation reflected from and/or transmitted by said sample to obtain a time domain waveform;
obtaining frequency data as a function of time from the time domain waveform;
deriving the representation from the frequency data.

Preferably the representation obtained is a three dimensional representation. The irradiation beam may be pulsed or continuous. It is also preferable that the sample is a pharmaceutical sample and the frequency data as a function of time is obtained using a Gabor transform. In this way, the frequency data obtained is time dependent.

The Gabor transform may be implemented using a windowed Fourier transform, a correlation of a specific kernel function or a filter-bank. The frequency, window type and/or window width of the Gabor function may be selected to optimise spectral or temporal features. Therefore regions containing resonance in the absorption spectrum may be avoided by selecting a kernel function frequency that lies in a region of low absorption within the sample.

In a preferred aspect, a method according to the present invention further comprises:
subdividing the sample to be imaged into a two-dimensional array of pixels,
detecting radiation from each pixel;
obtaining a time domain waveform for each pixels;
obtaining frequency data as a function of time for each pixel from the respective time domain waveforms;
deriving a representation as a function of depth at each pixel from the respective frequency data; and
combining the representations for each pixel into a three dimensional compositional distribution representation for the sample.

In another preferred aspect, a method according to the present invention further comprises:
subdividing the sample to be imaged into a two-dimensional array of pixels,
detecting radiation from each pixel;
obtaining frequency data as a function of time for each pixel from the respective time domain waveforms;
deriving a cross-sectional compositional representation from the respective frequency data.

According to a further aspect of the invention, there is provided an apparatus for creating a three dimensional compositional distribution representation of a chemical sample, the apparatus comprising:
emitter for irradiating the sample with radiation having a frequency in the range from 25 GHz to 100 THz;
detector for detecting radiation reflected from and/or transmitted by the sample at a plurality of pixels and producing a time domain waveform for each pixel;
means for obtaining frequency data as a function of time from the time domain waveform for each pixel;
means for deriving a compositional representation as a function of depth from the frequency data for each pixel; and
means for combining the representations for each pixel to generate the three dimensional compositional distribution representation.

Preferably the apparatus images a pharmaceutical sample and the means for obtaining frequency data obtains the frequency data by applying a Gabor transform to the time domain waveform for each pixel.

Any of the methods and apparatuses of the present invention may be used in a pharmaceutical manufacturing process.

These aspects of the invention enable a three dimensional compositional representation of a chemical sample to be obtained, through the combination of scanning the sample with Terahertz radiation and applying Gabor transform methods, to allow three dimensional compositional information to be extracted.

While time-frequency techniques such as Gabor transforms are known analytical tools, the use of Gabor transforms as a feature extraction tool, enabling a three dimensional image to be produced is considered unique.

Therefore the present invention combines the use of Terahertz imaging, which allows an object to be scanned to obtain depth information, and time-frequency analysis methods, such as a Gabor transform, in order to obtain frequency spectra for a particular scanned point over a particular range of time/depth. From this information three dimensional spatial resolution images can be obtained in a relatively short period of time. This makes the techniques suitable for use in pharmaceutical development and on-line production quality control.

BRIEF DESCRIPTION OF THE DRAWINGS

The present invention will now be described with reference to the accompanying Figures, in which:

FIGS. 10$a$, 10$b$, 10$c$ and 10$d$ illustrate three dimensional images of a tablet obtained by a Gabor transform approach, which show inhomogeneities and density variations at different frequencies.

DETAILED DESCRIPTION OF PREFERRED EMBODIMENTS

According to one embodiment of the present invention, a solid or semi-solid composition, such as a pharmaceutical tablet undergoes Terahertz spectroscopy. This Terahertz scanning may occur using the arrangement shown in FIG. 1.

Figure 1:
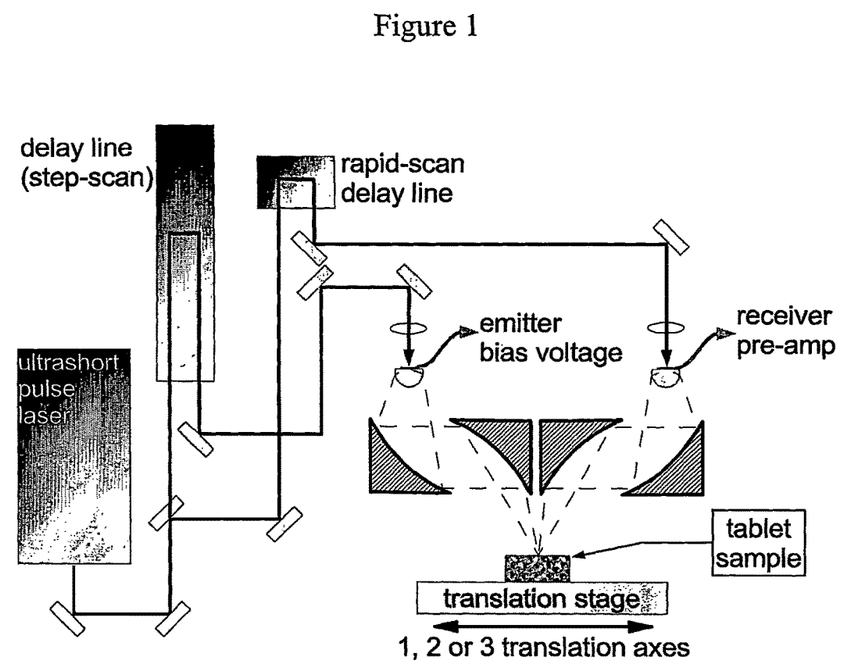
FIG. 1 illustrates an apparatus which can be used to image a sample.

The apparatus comprises an ultra-short pulse laser 11 which may be, for example, Ti:sapphire, Yb:Er doped fibre, Cr:LiSAF, Yb:silica, Nd:YLF, Nd:Glass, Nd:YAG or Alexandrite laser. This laser 11 emits pulses of radiation 13, such as a collimated beam of pulses, each of which comprise a plurality of frequencies. This pulse is reflected by first mirror 15 and second mirror 17 into beam splitter 19. The beam splitter splits the beam into a pump pulse 12 which is used to irradiate the sample and a probe pulse 14 which is used during detection.

The pump pulse 12 is directed into first scanning delay line 16. Scanning delay line 16 is a static delay, which adjusts the relative path-lengths between the pump and probe beams. The output pump pulse from the first scanning delay line is then directed by mirrors 18, 19, 40 and 41 into lens 20, which is preferably an aspherical glass lens, when used for NIR. Lens 20 focuses the pump pulse onto a source 21 which preferably comprises a frequency conversion member and a bow-tie emitter. The frequency conversion member is configured to mix the incident radiation in order to output radiation derived from the differences of the input frequencies, so-called difference frequency generation. This technique is described in more detail in GB 2 347 835.

The emitter 21 abuts a hyper-hemispherical lens 35. The terahertz beam that is output from the emitter 21 is directed by the first silicon hyper-hemispherical lens 35 towards a first parabolic mirror 25. The beam is then reflected off the first parabolic mirror 25 and onto second parabolic mirror 26, which directs the radiation onto sample 30. The sample may be replaced with a reference sample in order to remove background features from the final results. The radiation which is reflected from sample 30 is then collected by third parabolic mirror 27 and onto a fourth parabolic mirror 28 which directs the reflected radiation onto a second hyper-hemispherical lens 36 and onto a detector 29, such as a photoconductive detector. The pump beam 12 as reflected off the sample is re-combined with the probe pulse 14 at the receiver 29.

Prior to recombining with the pump beam 12, the probe beam 14 is directed into second scanning delay line 22 by mirror 42. This delay line is a rapid-scanning type and in its simplest form comprises two mirrors that serve to reflect the beam through a 180° angle. These mirrors are then quickly swept backwards and forwards in order to vary the path length of the pump pulse 12. Alternatively the second delay line could be a static delay line and the first delay line a scanning delay line, as the location of each type of delay line does not matter, provided the relative path lengths of the pump and probe beams can be matched.

The probe beam 14 output from the second scanning delay line 22 is then reflected off first probe beam mirror 23 onto second probe beam mirror 24 which directs the probe beam through lens 31, which is an aspherical glass lens when used to focus NIR beams. This lens 31 focuses the probe beam onto the receiver 29 for combining with the reflected pump beam.

The sample introduces a time delay in the path of the pump pulse. The delay is dependent on both the absorption coefficient and the refractive index of the sample. In order to obtain a detection signal, the frequency component of the probe beam must be in phase with a frequency component of the pump beam. Variation of the first and second scanning delay line allows the phase of the probe beam and/or pump beam to be swept with respect to the pump beam and/or probe beam and thus allows for measurement of the delay time of each frequency component which passes through the sample.

While the apparatus has been described in relation to pulses, such as a collimated beam of pulses, it is to be appreciated that the present invention may also be implemented using a continuous wave (CW) source. Continuous wave generation is described in detail in U.S. Pat. No. 7,174,037, which is incorporated herein by reference in its entirety.

This apparatus described can be utilised to obtain time domain data of a pharmaceutical sample using broadband phase-sensitive Terahertz radiation. To generate an image, measurements of the THz signal can be obtained from a number of different parts of the pharmaceutical sample. For example the area of the sample which is to be imaged is subdivided into a two dimensional array of pixels and the reflected radiation from each of the pixels is detected. This provides depth information for each pixel. The sample may be moved relative to the beam of radiation through the focal plane of the THz beam or the beam may be moved relative to the sample or both, to obtain this information. As shown in FIG. 1, the sample may be placed on a translation stage 32 to appropriately move the sample. This translation stage 32 could move the sample one dimensionally along one axis of movement or through two or three axes of movement.

An alternative embodiment of the invention, which is particularly useful for thick samples, focuses the THz beam within the tablet, rather than at a point on the sample surface, so that the time-domain signal is determined at that focal plane within the tablet. The position of the focal plane is generally chosen so that the region of interest in the sample is in focus. Outside the vicinity of the focal plane, features of the sample that are not of interest or are undesirable are reduced, such as top surface reflection.

The imaging signal obtained through this Terahertz imaging is dependent upon both time and frequency. To accurately represent this signal, according to the present invention, the signal is localised in time and frequency. This is achieved using time-frequency analysis such as by using a Gabor transform. The Gabor transform has good localisation in time and frequency is used to analyse the time-domain waveforms for each pixel.

The use of Gabor functions advantageously provides the ability to analyse a time domain signal over a particular period of time, and correspondingly over a particular depth, since the time domain signal obtained from the sample is in effect a measure over the depth of the sample. This is to be contrasted with standard Fourier transforms, which analyse a signal over all time (i.e. for an infinite duration) and has a good localisation in frequency but no localisation in time. The present invention, in seeking to create a three dimensional composition representation of a tablet therefore is based upon the recognition that localisation in time as well as frequency was required and that this could be provided by utilising time-frequency analysis, such as by using Gabor transforms.

For a window function, $g_{(b,\omega)}(t)=e^{i\omega t}g(t-b)$, where t represents time, $\omega$ is angular frequency and b a dummy variable, the Gabor transform is defined as $$G_f(b,\omega)=\int_{-\infty}^{\infty} f(t)\overline{g(t-b)}e^{-i\omega t}dt$$

where $\overline{g(t-b)}$ represents the complex conjugate. The window function g may be any function that is well localised in time and frequency. Some examples are those used in spectral analysis, including rectangular, triangular, Hanning, Hamming, Gaussian and Blackman.

The Gabor transform can be implemented in a number of ways, as a windowed Fourier transform, as a correlation of a specific kernel function with the time domain waveform or using a filter bank approach. In the filter bank approach the waveform is decomposed into separate frequency bands using a succession of filters.

Figure 2:
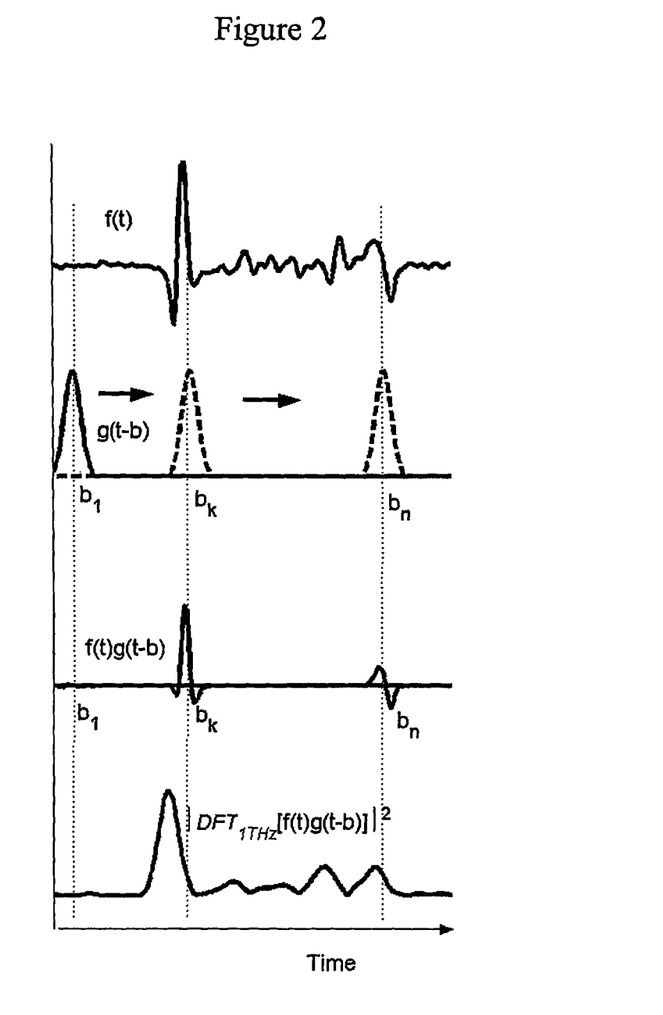
FIG. 2 illustrates the application of a windowed Fourier transform on a time domain waveform to generate a Gabor transform.

The windowed Fourier transform is accomplished by Fourier transformation, F, of the product of the selected time window, g with the THz time-domain waveform, f, for each translation of the window position, b $$G_{(\omega,b)}=|F[f(t)g(t-b)]|^2$$

This is illustrated in FIG. 2. The first graph is f(t), the time domain waveform and the second graph is of g(t-b), being a Gaussian window at several translations b. The third graph shows the multiplication of f(t) and g(t-b), which is effectively the addition of the first and second graphs. The final graph is that of the resultant windowed Fourier transform, which is achieved by obtaining by determining the modulus squared of the discrete Fourier transform of f(t)g(t-b), which is calculated at a specific centre frequency, $\omega$, for all window translations b, for all pixels in the THz image data set. In the illustrated graph, the discrete Fourier transform is calculated at 1 THz for all instances of the window function. Three-dimensional images from THz time-domain data, may then be obtained from this data.

The selected frequency, window type and width can be chosen to optimise either spectral or temporal features. Qualitatively, using a wider window in the time domain provides higher spectral resolution, whereas a shorter time window leads to better resolution of features in the time domain, with a corresponding compromise in spectral resolution.

Figure 3:
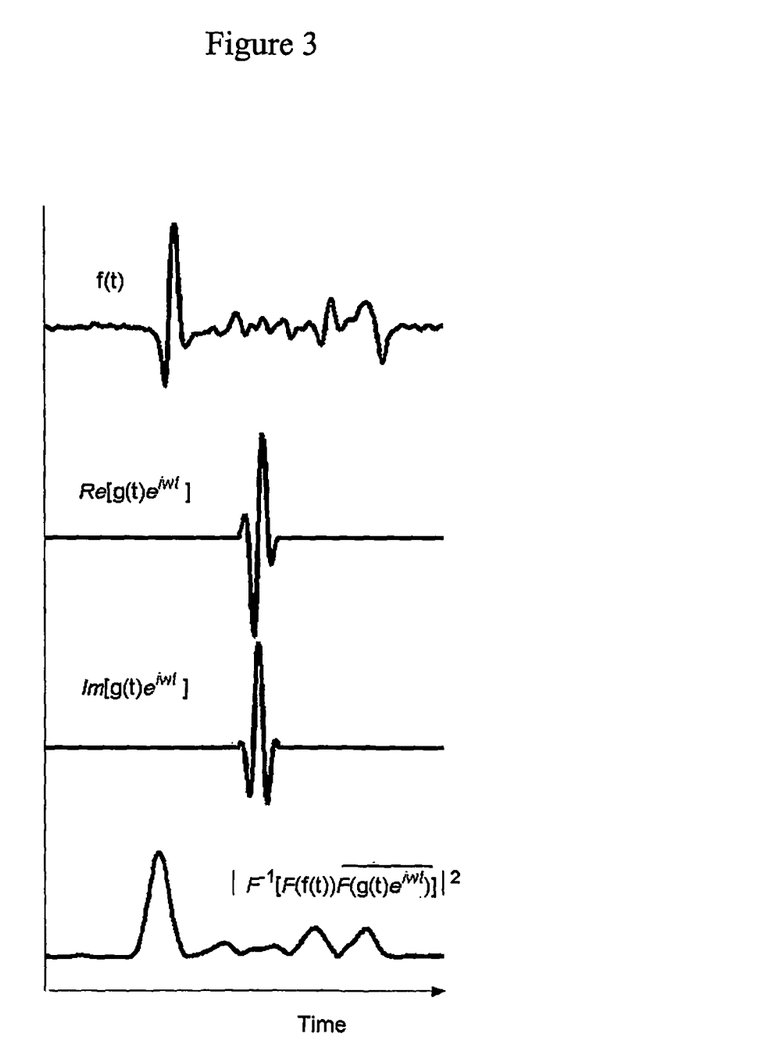
FIG. 3 illustrates the application of a kernel function on a time domain waveform to generate a Gabor transform.

An alternative mathematically equivalent method for obtaining the Gabor transform is the evaluation of the modulus squared of correlation of the THz time-domain waveform with the kernel function $g_{(\omega)}(t)=e^{i\omega t}g(t)$. An efficient implementation of the correlation is achieved by using the relationship for correlation $$G_{(\omega,b)}=|F^{-1}[F(f(t))\overline{F(g(t)e^{i\omega t})}]|^2$$

The determination of this is shown in FIG. 3. The first graph, as in FIG. 2, shows the time domain waveform. The second graph is of the real component of the kernel function $g_{(\omega)}(t)=e^{i\omega t}(t)$ and the third graph is of the imaginary component of this kernel function. The kernel function is a product of a window (in this case the same gaussian window used in FIG. 2), with a complex exponential at the desired frequency, 1 THz in this example. The final graph shows the result of the correlation implementation of the Gabor transform for this kernel function, which is clearly equivalent to the resultant transformation in the final graph of FIG. 2

The time domain waveform in the first graph of FIGS. 2 and 3 was obtained by imaging a polyethylene tablet with aspirin distributed throughout its volume. The resultant Gabor transforms in FIGS. 2 and 3 demonstrates features of the tablet. In the last graph in FIGS. 2 and 3 the first spike is due to the front surface of the tablet, while the last hump is due to the refractive index transition at the back surface of the tablet. Aspirin/polyethylene interfaces are illustrated by the various humps there between.

The Gabor transform can provide an entire spectrum for any particular windowed region of the time-domain waveform for a particular image pixel. It can therefore also be used to obtain spectra relating to different depths and regions within a tablet. The measured reflected pulses are a function of the material through which the THz radiation has passed, as well as the inhomogeneities and density fluctuations encountered. Thus the spectra will not only relate to the region windowed, but also be a function of the prior volume through which the radiation has traversed.

Figure 9:
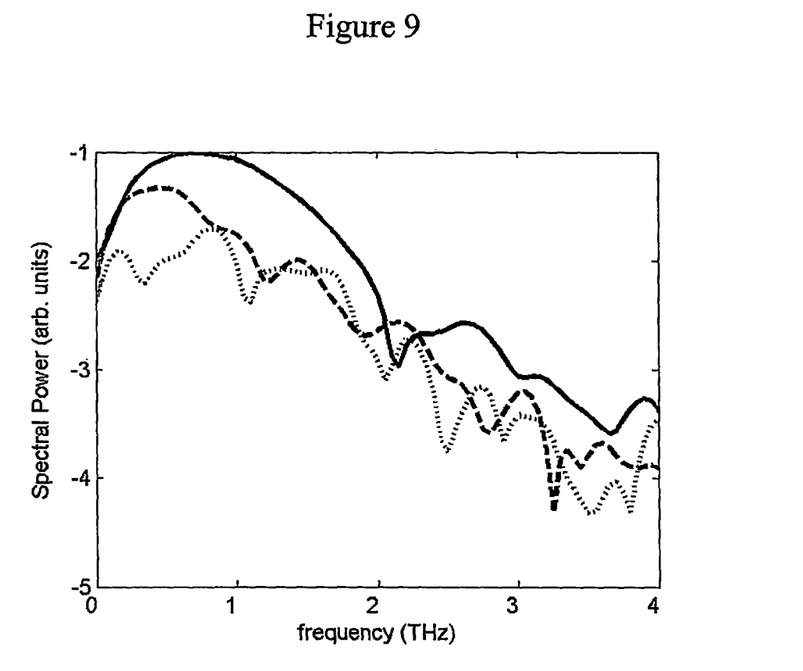
FIG. 9 illustrates spectra obtained from a Gabor transform of a pixel within a polyethylene/aspirin tablet at times/depths corresponding to the front tablet surface (full line), the aspirin/polyethylene interface (dotted line) and the back surface (dashed line)
Figure 10A:
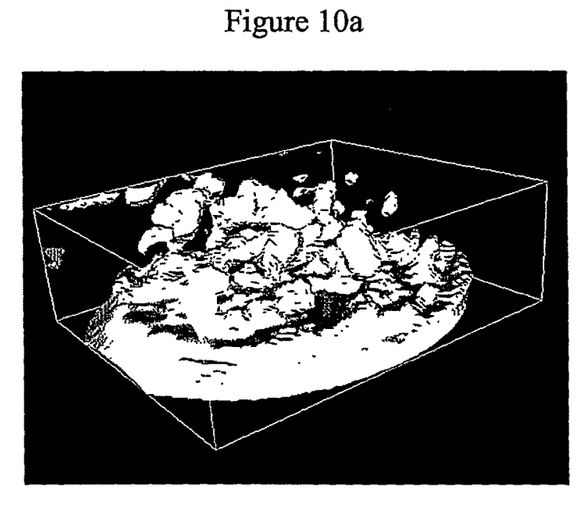
Figure 10B:
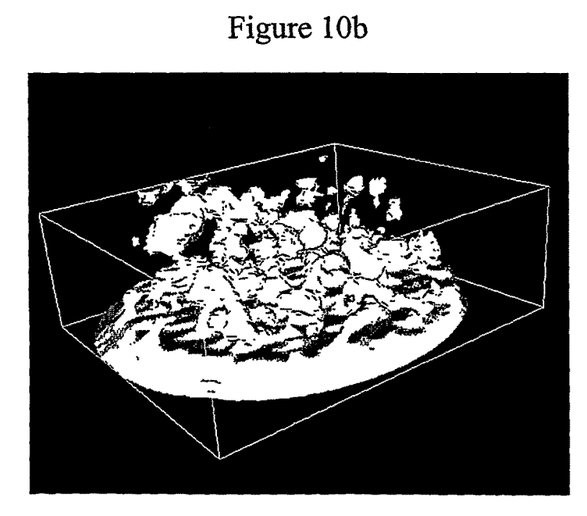
Figure 10C:
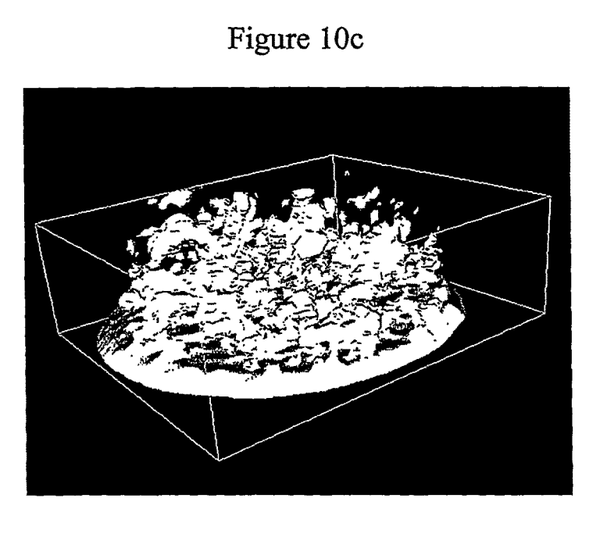
Figure 10D:
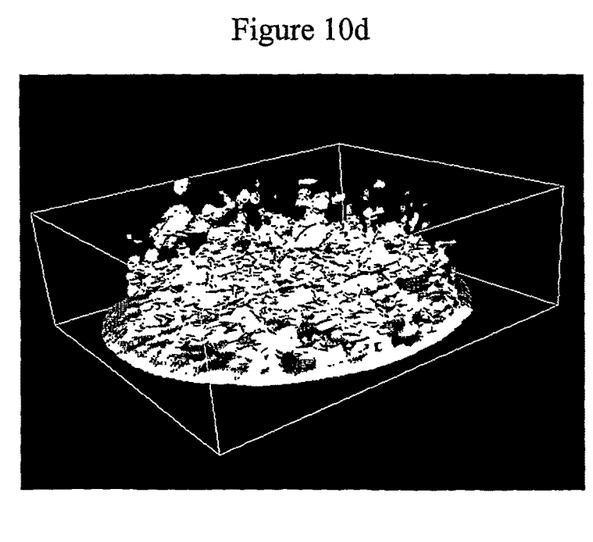

In this regard, FIG. 9 displays spectra obtained from different depths in the polyethylene-aspirin tablet. The full line illustrates spectra obtained from the Gabor transform at times/depths corresponding to the front tablet surface. The dotted line illustrates a corresponding spectra for the aspirin/polyethylene interface and the dashed line for the back surface. Therefore, this graph illustrates how the time-frequency technique can provide spectral information at depth within the tablet, which can provide information about the chemical nature of materials present and at the interfaces.

Figure 4:
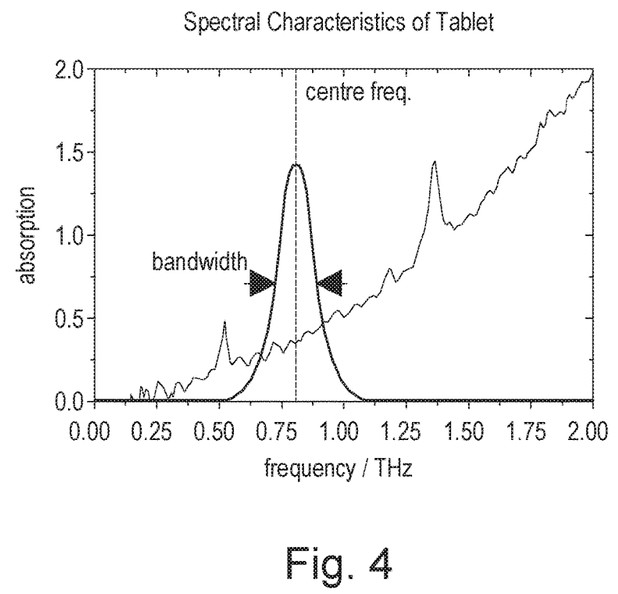
FIG. 4 illustrates the tuning of Gabor transform to avoid absorption peaks in tablet due to lactose.

FIG. 4 illustrate an absorption spectrum for an imaged lactose tablet with an example frequency-window superimposed. The graph shown of absorption as a function of frequency has a couple of spurious absorption peaks, at about 0.5 THz and 1.4 THz. It is desirable to analyse regions of low absorption within the tablet, as this occurs where the tablet transmits THz radiation. To tune the transform in order to avoid absorption peaks, a kernel function may be used. In FIG. 4, a Gaussian kernel function is illustrated. The centre frequency and width of the Gaussian kernel function can be chosen to maximise the contrast due to structural features or areas of inhomogeneity in the sample. For example, in FIG. 4 the centre frequency has been chosen to lie in a region of low absorption and to avoid the peaks in absorption. The centre frequency should also be chosen to avoid regions containing one or more instances of resonance in the absorption of THz by the sample.

Figure 5:
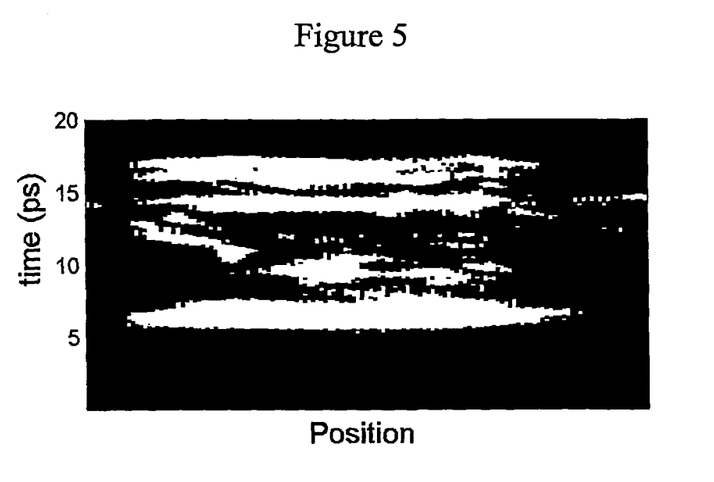
FIG. 5 illustrates a two dimensional B-scan (depth) view of a tablet with an aspirin layer, obtained by applying a Gabor transform to a time domain waveform obtained by scanning the tablet with Terahertz radiation.

Once the frequency domain data which is dependent upon time has been obtained for each pixel, such as in the last graph of FIGS. 2 and 3, the frequency data can be combined and depicted graphically, such as is shown in FIG. 5.

FIG. 5 illustrates a B-scan view, in terms of time against position (i.e. the position of each pixel in a row of pixels in the focal plane), of a polyethylene tablet with an aspirin layer. Time is a good approximation for depth, in that larger times correspond to deeper sections. The frequency at each time position for each pixel is represented by varying shades of light and dark. The lightest region at about 6 picoseconds on the y-axis is a surface layer of polyethylene. At about 17 picoseconds on the y-axis, another layer is discernible, which is the other surface layer of polyethylene. These layers are apparent in the image, due to reflections occurring due to the change of refractive index that occurs as the light passes from air into and out of the tablet as applicable. The light regions between these two surfaces are indicative of regions of aspirin in the tablet. The contrast is obtained by virtue of the THz pulse passing through the polyethylene and reflecting off the aspirin layer. This is represented by the white clumps between the surfaces. Hence the dark regions represent regions where no reflection occurs, or only a very small amount of reflection in comparison to the white regions. Therefore, aspirin may occur in some of the darker regions, but only in very small amounts.

The image in FIG. 5 was derived from a Gabor transform applied to the resultant time domain waveform for the imaged tablet. In the Gabor transform a Gaussian window was used, with a width of 1 picosecond and at a frequency of 1 THz.

Figure 6:
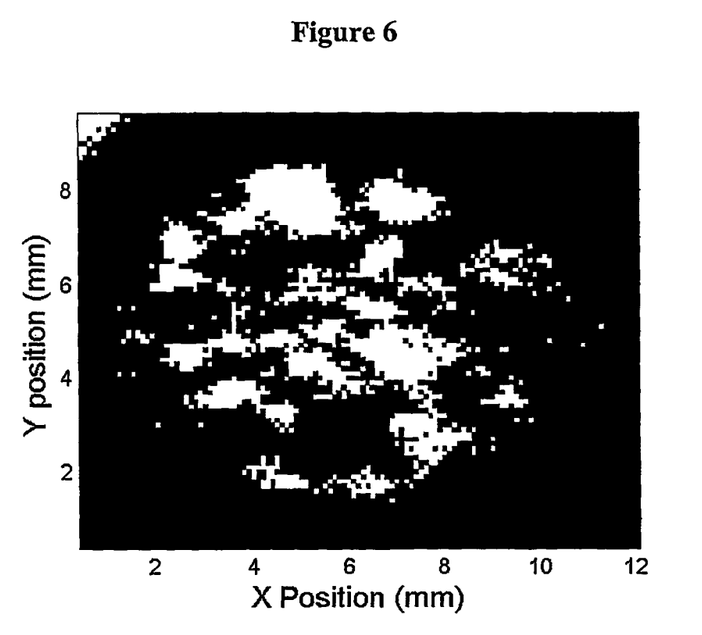
FIG. 6 illustrates a two dimensional C-scan (cross-sectional) view of the tablet imaged in FIG. 5.

FIG. 6 illustrates a C-scan view of the same polyethylene tablet of FIG. 5, in terms of x/y surface positions. The time that this cross-sectional image corresponds to is 9.6 ps. The round shape of the tablet is readily discernible, and the paler regions indicate areas of aspirin of varying concentrations.

Figure 11:
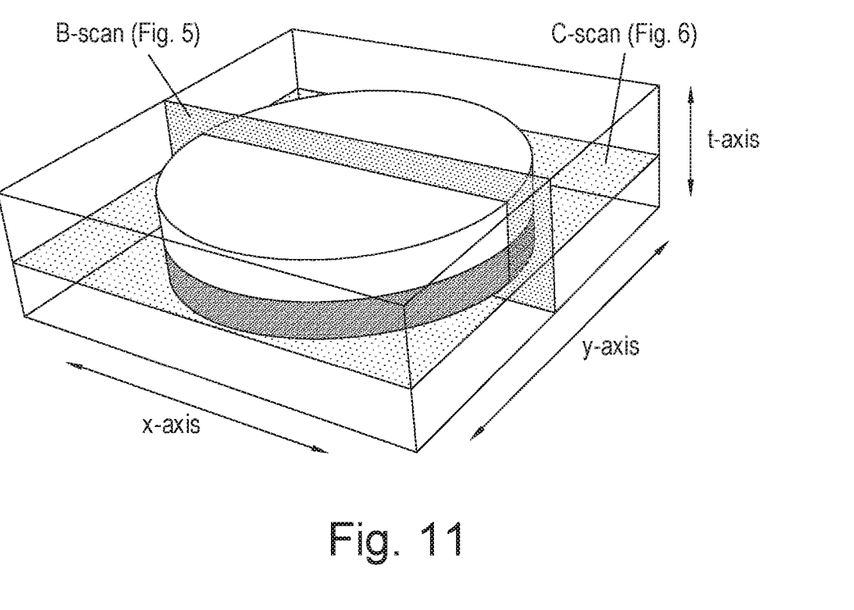
FIG. 11 illustrates the relationship between the B-scan view in FIG. 5 and the C-scan view of FIG. 6.

FIG. 11 illustrates the relationship between the B-scan view in FIG. 5 and the C-scan view of FIG. 6. This graph shows a three dimensional volume with the B-scan and C-scan views appropriately positioned.

Figure 7:
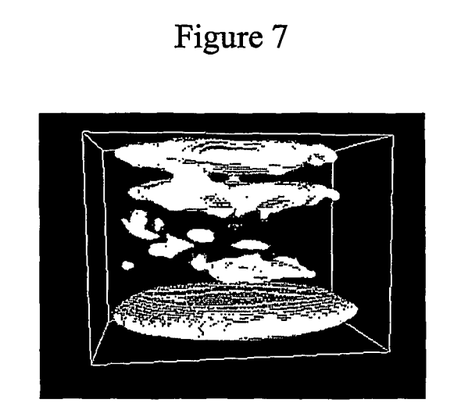
FIG. 7 illustrates a three dimensional image of the polyethylene tablet with aspirin, as used in FIGS. 5 and 6. This image was obtained using terahertz pulsed imaging (TPI) and the Gabor transform.

FIG. 7 illustrates a three dimensional illustration of the same polyethylene tablet of FIGS. 5 and 6. FIG. 7 provides a more complete view of the tablet composition of the main constituents. This graph can be obtained by combining the depth graphs, such as shown in FIG. 5 for all rows of pixels. Alternatively, FIG. 7 may be achieved by combining the cross-sectional graphs, such as shown in FIG. 6, within the tablet, from the top surface to the bottom surface. In FIG. 7 top and bottom layers of polyethylene are apparent, as well as a main intermediate layer of aspirin. This technique therefore provides a spatial representation of the tablet's constituents.

In the graphs of FIGS. 5, 6 and 7, it is possible to discern different constituents by virtue of different degrees of light and dark. This is due to changes in refractive index/absorption within the tablet leading to reflected THz pulses. These pulses show up in the Gabor transform time/depth profile as features. Hence, it is inhomogeneity and density variations and changes in structure that lead to these features.

Figure 8:
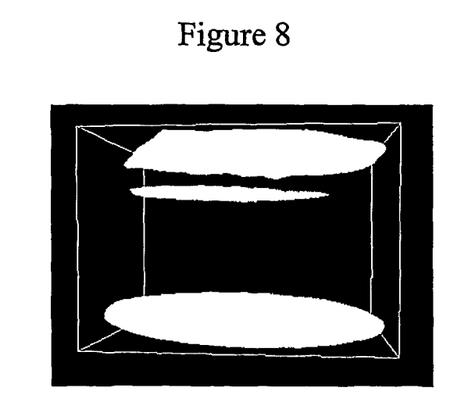
FIG. 8 illustrates a three dimensional image of a polyethylene tablet obtained using TPI and Gabor transform analysis.

FIG. 8 is an illustration of the same technique applied to a pure polyethylene tablet. That is, a time domain waveform was first obtained using terahertz pulsed imaging (TPI) for a plurality of pixels. The time domain data was then transformed to time dependent frequency domain using the Gabor transform as used for FIGS. 5 to 7. The image shows the top and bottom surface layers, due to the refractive index changes that occur in these areas, but no internal clumps. Hence, this graph shows that the clumps illustrated in FIG. 7 are due to the layer of aspirin included in that imaged tablet.

The Gabor transform can also provide three dimensional images indicating granularity. With reference to FIG. 10, four three dimensional images are provided, which were obtained using the Gabor transform approach, of a tablet made up of 20% lactose, 20% cellulose and 60% polyethylene compressed to 2 tonnes. This tablet was chosen as it was known to have an inhomogeneous granular structure. The image in FIG. 10a was obtained at a frequency of 0.35 Thz, the image at FIG. 10b at 0.45 Thz, the image at FIG. 10c at 0.64 Thz and the image at FIG. 10d at 0.84 Thz. The complete tablet is not illustrated for purposes of clarity. Instead, the surface at which the THz radiation was incident is at the bottom of the image, and the first few millimeters within the tablet are shown. From these images, it is apparent that the different frequencies at which the Gabor transform is applied affects the definition of the images.

The images in FIGS. 10a-d show the scale of the inhomogeneities in the tablet and were obtained by focussing within the sample to reduce surface signals and improve sensitivity to the smaller density fluctuations within the sample. Similar Gabor transform type analysis as was used in relation to FIGS. 7 and 8 was also used in relation to FIG. 10a-d. The different images that result, however, is mainly due to the two samples having different structures. That is, the sample shown in FIG. 7 has a compositional variation whereas the sample in FIG. 10 has an inhomogeneous granular structure. If a sample had both compositional and granular inhomogeneity, the resulting images would show contributions from both of these effects.

Figure 12:
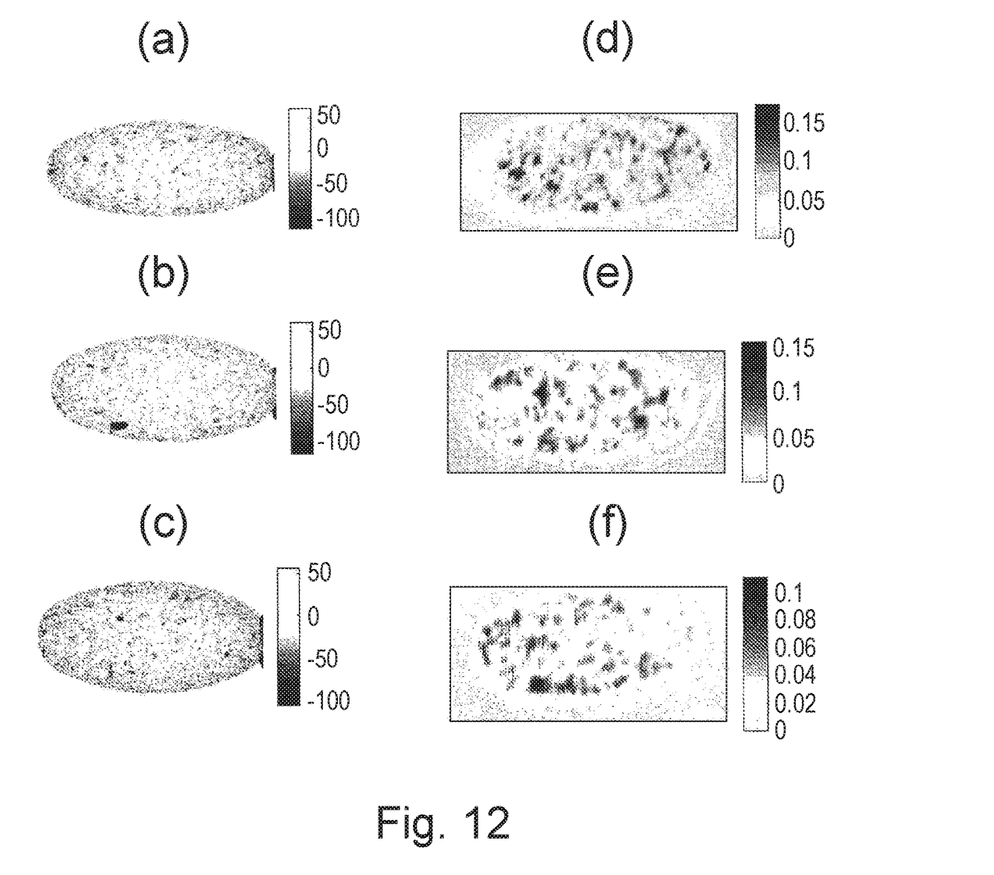
FIGS. 12a, 12b and 12c illustrate tablet composition images obtained using X-ray-CT
FIGS. 12d, 12e and 12f illustrate corresponding tablet composition images obtained using a technique embodying the present invention.

To illustrate the effectiveness of the present invention, a tablet composed of a number of excipients was imaged at three different depths using a Terahertz Pulse Imaging (TPI) technique embodying the invention and also using an existing technique, being X-Ray computed tomography (X-Ray-CT). FIG. 12 illustrates the results. Images at (a), (b) and (c) on the left of the Figure are the X-Ray-CT images at depths of 0.3 mm, 0.6 mm and 1.2 mm respectively. The images at (d), (e) and (f) on the right of the Figure are the TPI images of the tablet at depths of 0.3 mm, 0.6 mm and 1.2 mm respectively.

Comparing images (a) and (d) being the X-Ray-CT and TPI images respectively at a depth of 0.3 mm, it is apparent that similar features can be seen in both images, although a number of extra features can be seen in the TPI image. Similar results can be seen when comparing X-Ray-CT image (b) and TPI image (e), each at a depth of 0.6 mm and X-Ray-CT image (c) and TPI image (f), each at a depth of 1.2 mm. It is considered that the enhanced images obtained using TPI are due to the X-Ray-CT sensitivity being dependent only upon density changes in the tablet, whereas the TPI technique is sensitive to changes in the chemical nature of the tablet as well as density changes.

Alterations and additions are possible as will be apparent to the person skilled in the art. For example, while the present invention has been described in relation to standard round tablets, the techniques of this invention are equally applicable to other solid, semi-solid or granular dosage delivery forms to be administered orally or by other means. In addition, the present invention may be applied to any solid, semi-solid or granular chemical composition where analysis of the constituents is required.

Further, while the present invention has been described in relation to pharmaceutical development and manufacturing it is applicable to any field involving pharmaceutical analysis, including drug dosage management. For example, drug dosage management is an area of research concerned with mixing different drugs in a single dose and extending the period of drug release.

The invention claimed is:

1. A method of viewing compositional inhomogeneities in a solid chemical sample having a surface and a thickness, the method comprising:
   irradiating the sample with a first pulse of radiation having a plurality of frequencies in the range from 25 GHz to 100 THz;
   directing reflected and/or transmitted radiation from the sample onto a detector for combining with a second a second pulse of radiation, wherein at least one of the first and second pulses is delayed by a scanning delay line;
   detecting radiation with the detector, over time to obtain a time domain waveform, wherein variation of the scanning delay allows for measurement of a delay time, wherein the delay time, which forms an x-axis of the time domain waveform, relates to the depth in the sample at which the pulsed radiation beam was reflected, wherein the time domain signal is determined corresponding to a range of depths in a region of interest within the sample;
selecting a depth of the sample to analyze;
converting the time domain waveform, localized to the selected depth, from the time domain to the frequency domain using a time domain to frequency domain transform to obtain frequency data localized to the selected depth; and
determining the composition of all or part of the sample using the frequency data for the selected depth.

2. The method according to claim 1 wherein the sample is a pharmaceutical sample.

3. The method according to claim 1 wherein the composition of all or part of the sample is determined from an image generated by plotting the frequency data for the selected depth, wherein the image is a three dimensional representation of compositional distribution.

4. The method according to claim 1 further comprising:
subdividing the sample into a two-dimensional array of pixels, detecting radiation from each pixel;
obtaining a time domain waveform for each pixels;
obtaining frequency data as a function of time for each pixel from the respective time domain waveforms;
deriving an image as a function of depth at each pixel from the respective frequency data; and
combining the images for each pixel into a three dimensional compositional distribution image for the sample.

5. The method according to claim 1 further comprising:
subdividing the sample into a two-dimensional array of pixels,
detecting radiation from each pixel;
obtaining a time domain waveform for each pixel;
obtaining frequency data as a function of time for each pixel from the respective time domain waveforms; and
deriving a cross-sectional compositional image from the respective frequency data.

6. The method according to claim 1 as used in a pharmaceutical manufacturing process.

7. The method of claim 1, wherein determining the composition of all or part of the sample, comprises generating a representation of the composition of the sample, by plotting the frequency data for the selected depth.

8. The method of claim 1, wherein the pulses are reflected by at least a first mirror and a second mirror before passing into the beam splitter.

9. The method of claim 8, wherein the radiation is reflected by at least a third mirror and a fourth mirror before being directed onto the detector.

10. A method of viewing a granularity of a solid chemical sample having a surface and thickness, the method comprising:
irradiating the sample with a first pulse of radiation having a plurality of frequencies in the range from 25 GHz to 100 THz
directing the reflected and/or transmitted radiation from the sample onto a detector for combining with a second pulse of radiation, wherein at least one of the first and second pulses is delayed by a scanning delay line;
detecting radiation, with the detector, over time to obtain a time domain waveform, wherein variation of the scanning delay allows for measurement of a delay time, wherein the delay time, which forms an x-axis of the time domain waveform, relates to the depth in the sample at which the radiation was reflected;
selecting a depth of the sample to analyze;
converting the time domain waveform, localized to the selected depth, from the time domain to the frequency domain using a time domain to frequency domain transform to obtain frequency data localized to the selected depth; and
determining the granularity of all or part of the sample using the frequency data for the selected depth.

11. The method of claim 10, wherein determining the granularity of all or part of the sample, comprises generating a representation of the composition of the sample, by plotting the frequency data for the selected depth.

12. The method of claim 10, wherein the pulses are reflected by at least a first mirror and a second mirror before passing into the beam splitter.

13. The method of claim 12, wherein the radiation is reflected by at least a third mirror and a fourth mirror before being directed onto the detector.

14. A method of viewing compositional inhomogeneities in a solid chemical sample having a surface and a thickness, the method comprising:
irradiating the sample with a first pulse of radiation having a plurality of frequencies in the range from 25 GHz to 100 THz
directing the reflected and/or transmitted radiation from the sample onto a detector for combining with a second pulse of radiation, wherein at least one of the first and second pulses is delayed by a scanning delay line;
detecting radiation, with the detector, over time to obtain a time domain waveform, wherein variation of the scanning delay allows for measurement of a delay time, wherein the delay time, which forms an x-axis of the time domain waveform, relates to the depth in the sample at which the pulsed radiation beam was reflected, wherein the time domain signal is determined corresponding to a range of depths in a region of interest within the sample;
selecting a depth of the sample to analyze;
converting the time domain signal, localized to the selected depth, from the time domain to the frequency domain using a Gabor transform to obtain frequency data localized to the selected depth; and
determining the granularity of all or part of the sample using the frequency data for the selected depth.

15. The method of claim 14 wherein the Gabor transform is implemented using a windowed Fourier transform, a correlation of a specific kernel function or a filter-bank.

16. The method of claim 14 further comprising applying the Gabor function to the time domain waveform and selecting frequency, window type and/or window width of the Gabor function to optimise spectral or temporal features.

17. The method of claim 14, wherein determining the granularity of all or part of the sample, comprises generating a representation of the composition of the sample, by plotting the frequency data for the selected depth.

18. A method of viewing compositional inhomogeneities in a solid chemical sample having a surface and a thickness, the method comprising:
irradiating the sample with a first pulse of radiation having a plurality of frequencies in the range from 25 GHz to 100 THz
directing reflected and/or transmitted radiation from the sample onto a detector for combining with a second pulse of radiation, wherein at least one of the first and second pulses is delayed by a scanning delay line;
detecting radiation, with the detector, over time to obtain a time domain waveform, wherein variation of the scanning delay allows for measurement of a delay time, wherein the delay time, which forms an x-axis of the time domain waveform, relates to the depth in the sample at which the pulsed radiation beam was reflected, wherein the time domain signal is determined corresponding to a range of depth in a region of interest within the sample;

selecting a depth of the sample to analyze;

applying a window to the time domain waveform at the selected depth and converting the windowed time domain waveform to the frequency domain using a time domain to frequency domain transform to obtain frequency data localized to the selected depth; and determining the composition of all or part of the sample using the frequency data for the selected depth.

19. The method of claim 18, wherein determining the composition of all or part of the sample, comprises generating a representation of the composition of the sample, by plotting the frequency data for the selected depth.

* * * * *